United States Patent
Faul et al.

[11] Patent Number: 6,094,007
[45] Date of Patent: *Jul. 25, 2000

[54] OPTICAL TRACKING SYSTEM

[75] Inventors: Ivan Faul, Boulder, Colo.; Russell Dahl, Newbury Park, Calif.; Ronald M. Pasquini, Boulder, Colo.

[73] Assignee: Image Guided Technologies, Inc., Boulder, Colo.

[ * ] Notice: This patent issued on a continued prosecution application filed under 37 CFR 1.53(d), and is subject to the twenty year patent term provisions of 35 U.S.C. 154(a)(2).

[21] Appl. No.: 09/118,271

[22] Filed: Jul. 17, 1998

Related U.S. Application Data

[60] Provisional application No. 60/053,216, Jul. 18, 1997.

[51] Int. Cl.⁷ ..................................................... H01S 63/04
[52] U.S. Cl. .......................................... 313/512; 313/498
[58] Field of Search ...................................... 313/512, 498

[56] References Cited

U.S. PATENT DOCUMENTS 5,931,570  8/1999  Yamuro ................................... 313/512

*Primary Examiner*—Vip Patel
*Attorney, Agent, or Firm*—Lowe Hauptman Gopstein Gilman & Berner

[57] ABSTRACT

An assembly adapted to emit electromagnetic radiation made up of an emitter of electromagnetic radiation; a non-reflective ceramic support for the emitter; a substantially transparent crown mounted on the support to define and enclose a space that houses the emitter; and leads attached to the emitter through the support. The combination of the non-reflective support and the transparent crown, and the location of the emitter in the enclosed space enables the emitter to emit electromagnetic radiation in a conical radiation pattern. The radiation pattern appears to have a centroid. This centroid appears to be in a more constant spatial position regardless of the viewing angle as compared with the apparent position of this centroid with other assemblies.

16 Claims, 1 Drawing Sheet

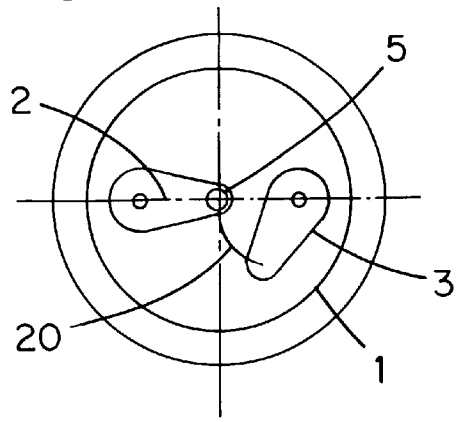
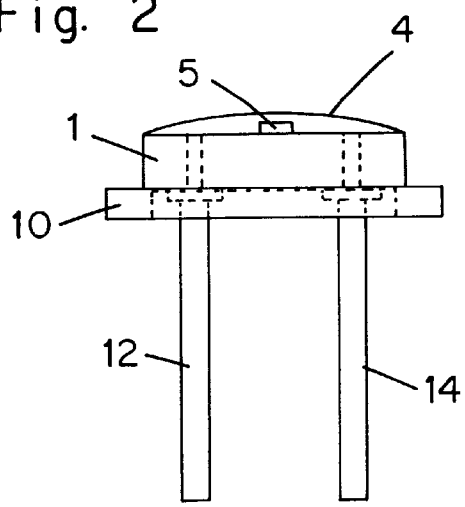
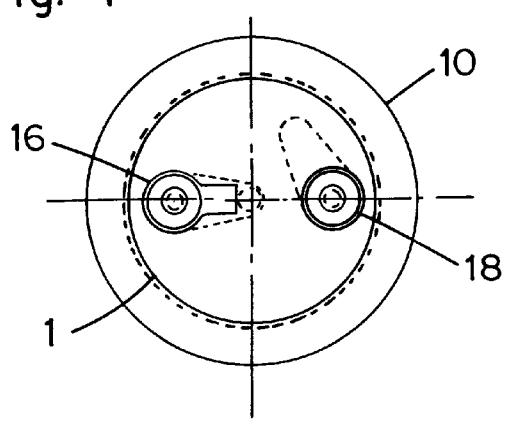

OPTICAL TRACKING SYSTEM

This is a continuation in part of Provisional application Ser. No. 60/053,216 filed on Jul. 18, 1997.

This invention relates to a system for locating and/or tracking the position and orientation of a body in three dimensional space. It more particularly refers to the use of an improved electromagnetic radiation emitter as a means of improving the accuracy of locating the object in space and digitizing its position and orientation.

BACKGROUND OF THE INVENTION

Several systems are known by which the locations of points in space can be identified and digitized. If these points are disposed on an object, and the size and shape of the object are predetermined or are known, it is possible to calculate the position and orientation of the object from knowing the locations of these several points on the object. In advanced systems, the position and orientation of a plurality of objects can be determined both independently with respect to the three dimensional space in which each object resides, and with respect to the other object(s). It is even possible, by frequent sampling of the locations of at least two points on an object, to track movement of the object, both absolutely with respect to the three dimensional space and relative to the position and orientation, and even movement of other objects(s) in the same space.

In one embodiment of these known systems, a plurality of emitters of electromagnetic radiation, such as light of a given wavelength, are fixed to the surface of at least one object. If it is desired to know the absolute positions and orientations of the objects being determined, the radiation emitted by the emitters can be received by a plurality of cameras, or other receivers which are in a known position in the three dimensional space. If, on the other hand, it is only desired to determine the position and orientation of the several objects relative to each other, the cameras do not need to be in known or fixed positions relative to the three dimensional space in which they reside, although they must still be in known relationship to each other. The radiation from the emitters to the receivers form straight lines and the angles that these ray lines make with respect to each other or with respect to predetermined reference lines or planes, respectively, can be used to compute the location of each radiation emitter in space. The location of each radiating emitter can be digitized, and all of the determined locations can be used to calculate the position and the orientation of the object in space.

It is desirable to use computers to assist in the calculation of the geometric relationships which derive the locations of the emitters. Therefore, the output of the camera systems that are used is preferably fed to a digital computer for calculating the necessary angles and digitized point source locations, and for converting these to the position and orientation of the object on which the emitters reside. The geometric calculations, and the algorithms that control these calculations do not form a part of this invention.

The accuracy of determining the location of the emitters is in great measure a function of the stability of the emitting point. One type of emitter that has been used with considerable success is a light emitting diode, an LED. In actual practice, the best LEDs have been those that emit light in the infra red spectrum. Since the mensuration device being discussed here has great utility in hospital operating rooms, the use of "invisible" light beams has an added advantage of not distracting the surgeon from his work. Light, with wavelengths in the visible spectrum, is typically filtered out by the optical sensor(s) to reduce interference with the "invisible", or infrared, radiation.

Optical emitters are generally housed in an assembly which protects them from dirt and other external influences. Part of this protection is commonly provided by a relatively clear crown over the emitter and a support (header) affixed to the object on which the emitter rests. The crown is normally mounted to the support, and the emitter (the LED chip) is generally centrally located on the support under the crown. Radiation is emitted from the emitter in substantially all hemispherical directions; from a direction normal to the surface on which the emitter is affixed to a direction substantially parallel or tangent to that surface. So long as the line of sight between the emitter and the camera approaches the tangent, the crown tends to make the optical location of the centroid of the emitter appear to move due to refraction of the radiation. Therefore, the camera "sees" the emitter at a place where it is not. While it is true that the dislocation of the apparent location of the emitter from the real location of the emitter is small, the resultant system inaccuracy can be very substantial. This is of particular importance when very accurate determinations of the positions and orientations of objects in space, such as surgical instruments, is being determined. It is not possible to be too accurate in determining the real location of the emitters so as to be able to very accurately determine the true position and orientation of the body on which the emitters reside. Put another way, the optical center of the emitter must appear to the camera to be in the same relative location regardless of the angle through which the emitter is viewed.

OBJECTS AND SUMMARY OF THE INVENTION

It is therefore an object of this invention to provide a mounted emitter of electromagnetic radiation that shows a substantially constant centroid of radiation over a wider viewing angle than has been possible in the past.

It is another object of this invention to provide an enhancement for a system for determining the location of points in space which has greater accuracy than has been possible in the past.

Other and additional objects will become apparent from a consideration of this entire specification, including the drawing hereof.

In accord with and fulfilling these objects, one aspect of this invention is a novel electromagnetic emitter which shows an apparent centroid of radiation that is substantially invariant over a wider solid angle than has been possible in the past. This is accomplished by mounting the emitter on a ceramic support that is substantially non-reflective of the electromagnetic ray energy being emitted. The non-reflectance of the ceramic support may take the form of the support being made of a material that is substantially fully transparent to the emitted electromagnetic radiation. It also may take the form of the support that is made of a material that is substantially fully absorptive of the energy being radiated by the emitter. Another characteristic of the electromagnetic emitter of this invention is that the electrical component leads do not protrude above the ceramic support surface. By using such a ceramic support without protruding pins or leads, it is possible to use a substantially flatter transparent crown as well as to prevent, or at least reduce interference and shadowing by the protruding pins and/or leads. It is preferred to use a transparent crown that is in the form of a solid arch, most preferably a hemispherical arch.

A spherical arch crown is based on a section of a sphere having its center substantially coincident with the emitter and a diameter that is substantially the length of a straight line from one edge of the support to the opposite edge of the support and passing through the emitter. Alternatively, it has been found to be quite satisfactory to use a flat crown, or in fact a crown of substantially any shape. In the event that a crown that is not a hemispherical arch is used, it is preferred that the emitter chip be disposed as close as possible to the crown. This reduces the refraction wandering of the apparent centroid of the emitted radiation.

By way of contrast to a hemispherical arch, a bow arch crown is based on a section of a sphere having a center that is not coincident with the emitter and a diameter that is substantially longer than the length of a straight line extending between opposite edges of the support and passing through the emitter. The crown bow arch is made flatter by increasing the diameter of the sphere of which the bow arch is a section, and by moving the center of the sphere further away from the crown. By flattening the transparent crown, the size, and particularly the height, of the emitter assembly is substantially reduced. In the ultimate, it is within the scope of this invention to use a substantially flat crown.

The electromagnetic radiation radiated from the emitter is generally conical in shape. Within that conical radiation, there is a centroid of radiation that is "seen" by suitable radiation detectors (e.g. cameras). In the prior art that used higher profile emitter assemblies and used support members thereof that reflected at least a portion of the electromagnetic radiation, the apparent centroid of radiation had the tendency to move as the angle through which the emitted radiation was viewed changed. Thus, the centroid of radiation appeared in one place when viewed from directly overhead. The apparent place of the centroid then changed as the viewing position proceeded from directly overhead toward the horizon.

The import of the instant invention is that when the emitter assembly is constructed as set forth herein, the centroid of radiation appears to be more stable. That is it remains in substantially the same place in space regardless of the angle from which it is viewed.

BRIEF DESCRIPTION OF THE DRAWING

Understanding of this invention will be assisted by reference to the drawing in which:

FIG. 1 is a bottom view of a light emitting diode according to this invention;

FIG. 2 is a side view of the light emitting diode of FIG. 1; and

FIG. 3 is a plan view of the same light emitting diode.

DETAILED DESCRIPTION OF THE INVENTION

Referring now to the drawing, wherein all like parts bear the same reference numbers, a non-reflective ceramic support 1 is disposed on a suitable mounting flange 10. Electrical leads 12 and 14 extend up to the support 1. An anode pad 2 of the emitter chip 5 is attached to one of the electrical leads 12. The other electrical lead 14 is attached to the cathode pad 3 of the emitter chip 5 by means of a bond wire 20. The anode and cathode can be reversed in position. The chip is preferably optically centered, as shown at 5, on the non-reflective ceramic support 1.

In the prior art, high profile bonding pins were used to affix the anode and the cathode to the support and to the electrical leads. This required the transparent dome to have a high crown that caused a dispersing lens effect to be created. This interfered with the integrity of the cone of the radiation pattern. In the design according to the instant invention, the high profile pins that were employed in the prior art are not used. Rather, according to this invention, the anode connection is a small flat tab, suitably a metallized film, that is disposed directly on the surface of the support 1. The emitting chip 5 is bonded directly to the anode tab surface 2. The cathode connection is a similar tab structure that is bonded directly to the surface of the support such that the bond wire 20 extends between the cathode pad and the cathode in a flattened, low profile, arc. This structure permits the transparent crown 4, which is suitably made of an optical grade transparent epoxy resin, but can be made of any other material that is substantially transparent to the electromagnetic radiation being emitted from the chip, to be substantially flattened into a bow arch of very low profile. The low profile of the crown 4 coupled with the non-reflectiveness of the support 1 and the low profile of joining pins make the observed apparent centroid of radiation stay in a substantially constant optical spot through all but the most extreme angles through which it is viewed.

The support is made of a non-reflective material that is coordinated in its transmission and absorption properties with the nature of the radiation being emitted. Where the emitted radiation is at a wavelength of 880 nm, a ceramic that is mostly aluminum oxide, preferably at least about 94% aluminum oxide, has been found to be very effective in either absorbing or transmitting, but not reflecting, radiation of this wavelength. In any case, this ceramic material does not reflect a substantial portion of incident radiation at the 880 nm wavelength. This causes great stability in the apparent location of the optical centroid of the emitted cone of radiation. Other supports, particularly other ceramic supports, will show similar non-reflectivity with respect to radiation of other wavelengths, as will be apparent to those of ordinary skill in this art. Similarly, other crown materials that are substantially transparent to the particular wavelength of radiation can be used to advantage.

According to this invention, it is preferred that the support used collectively absorb and/or transmit at least about 95% of the radiation of the desired wavelength. Where the reception properties of the radiation receiver are closely keyed to a specific wavelength of radiation, the transmission and absorbence of the support and the transmission of the crown should be considered from the perspective of the particular wavelength being radiated. Thus, if the receiver "sees" only 880 nm, it will not matter if the support reflects radiation of other wavelengths. The receiver will not "see" these other reflected wavelengths and therefore the centroid of the key wavelength, e.g. 880 nm, will not interfere with the sight of the important centroid The structure and composition of the components of this invention have served to reduce the background reflections from the support. They have stabilized the apparent optical position of the centroid of radiation from the diode chip. The omission of high profile mounting pins has reduced physical blockage of chip radiation and has eliminated, or at least minimized, other possible reflective surfaces. All of these attributes have combined to make it possible to locate the centroid of radiation in a far more accurate manner. This, in turn, makes for a more accurate determination of the location of the emitter chip. Since it is the summation of the locations of the emitter chips that determines the position and orientation of the object on which these chips are disposed, more accurate determination of the location of the centroid of radiation from a chip makes for a more accurate determination of the position and orientation of the object on which the chip is mounted.

What is claimed is:

1. An assembly adapted to emit electromagnetic radiation comprising:

an emitter of electromagnetic radiation;

a ceramic support for said emitter, wherein the material of said support does not reflect substantial amounts of said emitted radiation;

a crown mounted on said support and forming a juncture with said support, wherein said crown is substantially transparent to said electromagnetic radiation, and wherein the combination of said crown and said support define and enclose a space that houses said emitter;

wherein the combination of said non-reflective support and said transparent crown and the location of said emitter in said enclosed space enable said emitter to emit said radiation in a beam of substantially conical shape and wherein said beam comprises an apparent centroid that is disposed within the space defined by said support and said crown; and leads attached to said emitter through said support at points no further from the apex of said conical radiation beam than said centroid.

2. An assembly as claimed in claim 1 wherein said support is substantially transparent to said electromagnetic radiation.

3. An assembly as claimed in claim 1 wherein said support is substantially absorptive of said electromagnetic radiation.

4. An assembly as claimed in claim 1 wherein said crown comprises a substantially transparent epoxy resin.

5. An assembly as claimed in claim 1 wherein said emitted electromagnetic radiation is at substantially 880 nm and said support comprises mostly aluminum oxide.

6. An assembly as claimed in claim 1 wherein said emitter is a light emitting diode (LED).

7. An assembly as claimed in claim 2 wherein said support transmits at least about 95% of said electromagnetic radiation.

8. An assembly as claimed in claim 3 wherein said support absorbs at least about 95% of said electromagnetic radiation.

9. An assembly as claimed in claim 1 wherein said leads are attached to said emitter at points remote from said crown.

10. An assembly as claimed in claim 1 further including pins joining said emitter to said support.

11. An assembly as claimed in claim 10 wherein no substantial portion of said pins are disposed on the side of said emitter directed toward said crown.

12. An assembly as claimed in claim 11 wherein said pins are of a height such that they do not extend beyond said emitter into space defined by said crown.

13. An assembly as claimed in claim 1 wherein said crown is the shape of an hemispherical and wherein said emitter is disposed at the substantial enter of said spherical arch.

14. An assembly as claimed in claim 5 wherein said support comprises at least about 94 weight percent aluminum oxide.

15. An assembly as claimed in claim 1 wherein said crown is substantially flat.

16. An assembly as claimed in claim 1 wherein said emitter is disposed proximate to said crown.

* * * * *